US008158063B2

(12) United States Patent
Chiu et al.

(10) Patent No.: US 8,158,063 B2
(45) Date of Patent: Apr. 17, 2012

(54) BIOSENSOR PACKAGE STRUCTURE WITH MICRO-FLUIDIC CHANNEL

(75) Inventors: Chin-Fong Chiu, Taipei (TW); Ying-Zong Juang, Taipei (TW); Hann-Huei Tsai, Taipei (TW); Chen-Fu Lin, Taipei (TW)

(73) Assignee: National Chip Implementation Center National Applied Research Laboratories, Hsinchu (TW)

( * ) Notice: Subject to any disclaimer, the term of this patent is extended or adjusted under 35 U.S.C. 154(b) by 343 days.

(21) Appl. No.: 12/333,990

(22) Filed: Dec. 12, 2008

(65) Prior Publication Data

US 2010/0098585 A1 Apr. 22, 2010

(30) Foreign Application Priority Data

Oct. 20, 2008 (TW) ............................... 97140213 A

(51) Int. Cl.
*G01N 15/06* (2006.01)
*G01N 33/00* (2006.01)

(52) U.S. Cl. ........... 422/68.1; 422/63; 422/67; 702/100; 702/104; 702/116; 439/190; 73/37

(58) Field of Classification Search .................... 422/63, 422/67, 68.1; 702/100, 104, 116; 439/190; 73/37
See application file for complete search history.

(56) References Cited

U.S. PATENT DOCUMENTS 6,821,819 B1 * 11/2004 Benavides et al. ............ 438/122
7,375,404 B2 * 5/2008 Park et al. ...................... 257/414
7,410,616 B2 * 8/2008 Santini et al. ................. 422/101
7,419,639 B2 * 9/2008 Osterfeld et al. ............. 422/100
2002/0099359 A1 * 7/2002 Santini et al. ................. 604/521
2004/0151629 A1 * 8/2004 Pease et al. .................. 422/68.1
2005/0272169 A1 * 12/2005 Griffin et al. ................. 436/514
2009/0036328 A1 * 2/2009 Lee et al. ........................ 506/39

FOREIGN PATENT DOCUMENTS

TW I252839 2/2004

* cited by examiner

*Primary Examiner* — Brian J Sines
(74) *Attorney, Agent, or Firm* — Stites & Harbison, PLLC; Juan Carlos A. Marquez, Esq

(57) ABSTRACT

A biosensor package structure with a micro-fluidic channel is provided. The biosensor package structure includes a substrate, a biochip, and a cover. The substrate has a first surface, a second surface, and an opening. The biochip is attached on the first surface. A bio-sensing area of the biochip is exposed to the opening of the substrate. The cover is attached on the second surface to cover the opening so as to form a micro-fluidic channel. By implementing the invention, the manufacturing process of the biosensor is simplified and the productivity is increased.

10 Claims, 6 Drawing Sheets

BIOSENSOR PACKAGE STRUCTURE WITH MICRO-FLUIDIC CHANNEL

BACKGROUND OF THE INVENTION

1. Technical Field

The present invention relates to biosensor package structures with a micro-fluidic channel, and more particularly to a biosensor package structure with a micro-fluidic channel applicable to bioassay of biomedical samples.

2. Description of Related Art

Recently, in response to the progress of biotechnology, micro-electro-mechanical systems (MEMSs) have been developed to downsize otherwise large biochemical analysis instruments and integrate the microminiaturized biochemical analysis instruments into small chips, so as to reduce consumption of biomedical samples, avoid errors out of human operation, speed up assay processes, and improve assay accuracy.

A known technology in the art refers to the disclosure of Taiwan Patent No. I252839 for a manufacturing method of a microchip and the microchip manufactured by the method. Therein, the microchip comprises a substrate, a photoresist layer, an electrode unit, and a panel.

The photoresist layer is formed on the surface of the substrate while including a recess unit and a channel unit, wherein the recess unit has a plurality of recesses extending from the surface of the photoresist layer toward the substrate, and the channel unit includes a plurality of channels extending from the surface of the photoresist layer toward the substrate.

The electrode unit comprises a plurality of electrodes. Each of the electrodes has a contact portion and a control portion, wherein the contact portion is formed between the substrate and the photoresist layer while the control portion extends toward the periphery of the substrate and is exposed to the photoresist layer. Moreover, a portion of the electrodes have their contact portions exposed to corresponding said channels while the other electrodes have their contact portions corresponding in position to respective liquid tanks. A voltage is applied to the contact portion of each said electrode to form an electric field acting around the recess unit and the channel unit.

The panel is closely affixed to the photoresist layer so as to form each said liquid tank together with each said recess of the recess unit for accommodating a liquid, and form a micro-fluidic channel together with each said channel of the channel unit for allowing the liquid to flow therethrough.

When the electric field is formed by applying a voltage to the electrodes, the liquid in the liquid tanks corresponding in position to the electrodes is delivered to a predetermined liquid tank through the corresponding micro-fluidic channels under the effect of the electric field. When flowing in the micro-fluidic channel, the liquid is in contact with the contact portion of the electrode corresponding in position to the micro-fluidic channel.

To manufacture the microchip, a conductive adhesive is formed on the substrate by screen printing so as to function as the electrode unit, and the photoresist layer with a plurality of micro-fluidic channels is formed on the substrate and the electrode unit by lithography. Finally, by pressing and attaching the panel to the photoresist layer, the microchip is accomplished.

However, the conventional microchip structure entails complex processing procedures such as the aforesaid screen printing technology for forming the conductive adhesive on the substrate, physical coating processes, chemical coating processes, or combinations thereof to form the electrodes, but also requires an advance layout of masks before forming the photoresist layer with the micro-fluidic channels by lithography. Therefore, the conventional microchip structure is disadvantageous by its specific design and complex manufacturing processes and thus is unsuitable for mass production.

SUMMARY OF THE INVENTION

The present invention discloses a biosensor package structure having a micro-fluidic channel, wherein a simple packaging process is implemented to package the biosensor having the micro-fluidic channel, so as to simplify manufacturing process of the biosensor and increase the stability as well as reliability of the biosensor.

The present invention also discloses a biosensor package structure with a micro-fluidic channel, such that the biosensor having the micro-fluidic channel is fabricated, using packaging materials readily available, so as to reduce manufacturing costs of the biosensor.

To achieve these and other objectives, the biosensor structure of the present invention includes a substrate having a first surface, a second surface, and an opening, a biochip attached on the first surface and defined with a bio-sensing area exposed to the opening, and a cover attached on the second surface to cover the opening so as to form a micro-fluidic channel.

By implementing the present invention, at least the following progressive effects are achieved:

1. A biosensor is packaged by packaging technology, so as to simplify the manufacturing process of the biosensor and enhance stability and reliability of the biosensor.

2. A biosensor is fabricated, using packaging materials readily available, so as to reduce the manufacturing costs of the biosensor.

BRIEF DESCRIPTION OF THE DRAWINGS

The invention as well as a preferred mode of use, further objectives and advantages thereof, will best be understood by reference to the following detailed description of illustrative embodiments when read in conjunction with the accompanying drawings, wherein.

DETAILED DESCRIPTION OF THE PREFERRED EMBODIMENTS

Figure 1:
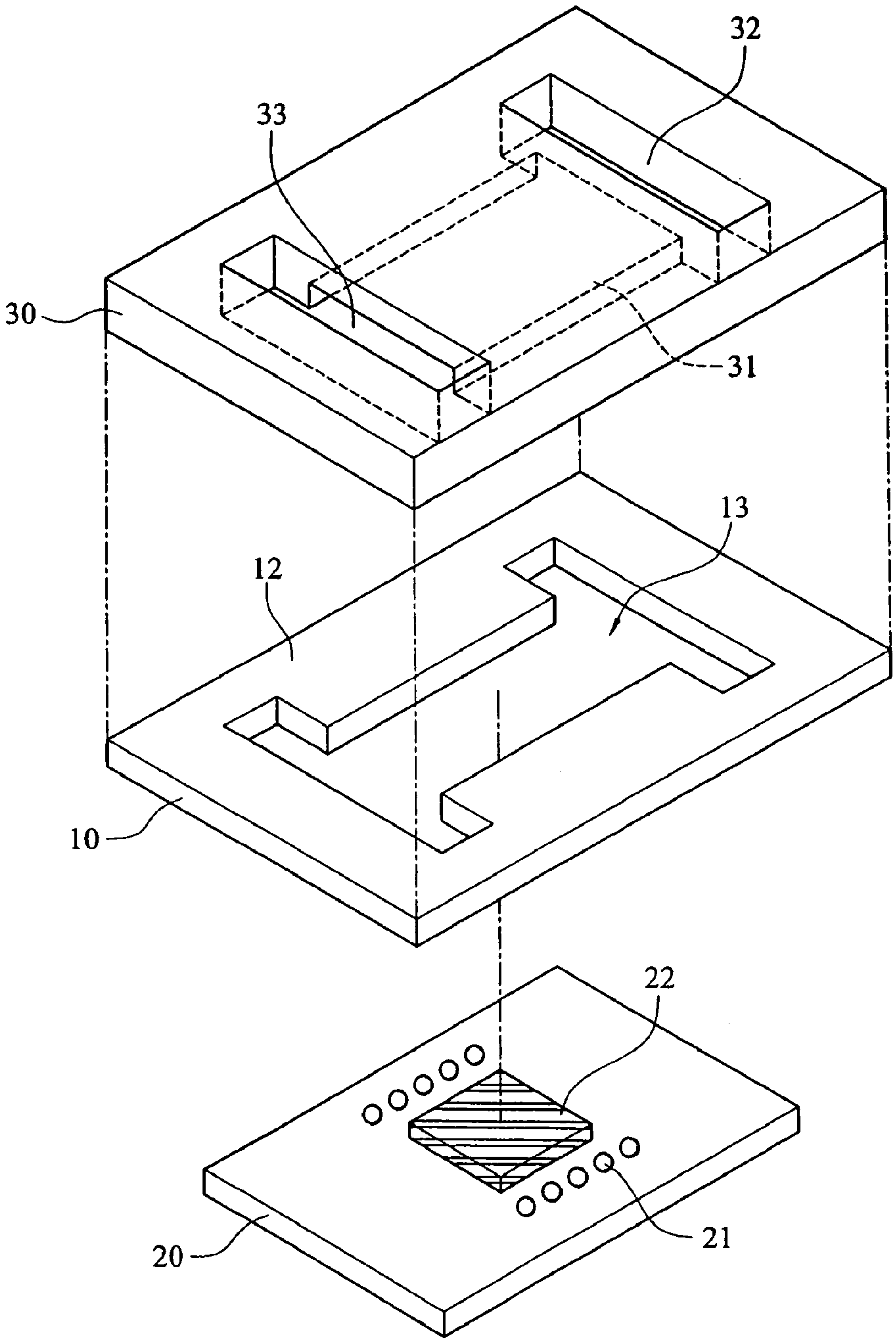
FIG. 1 is an exploded view of a biosensor package structure with a micro-fluidic channel according to a first embodiment of the present invention.
Figure 2:
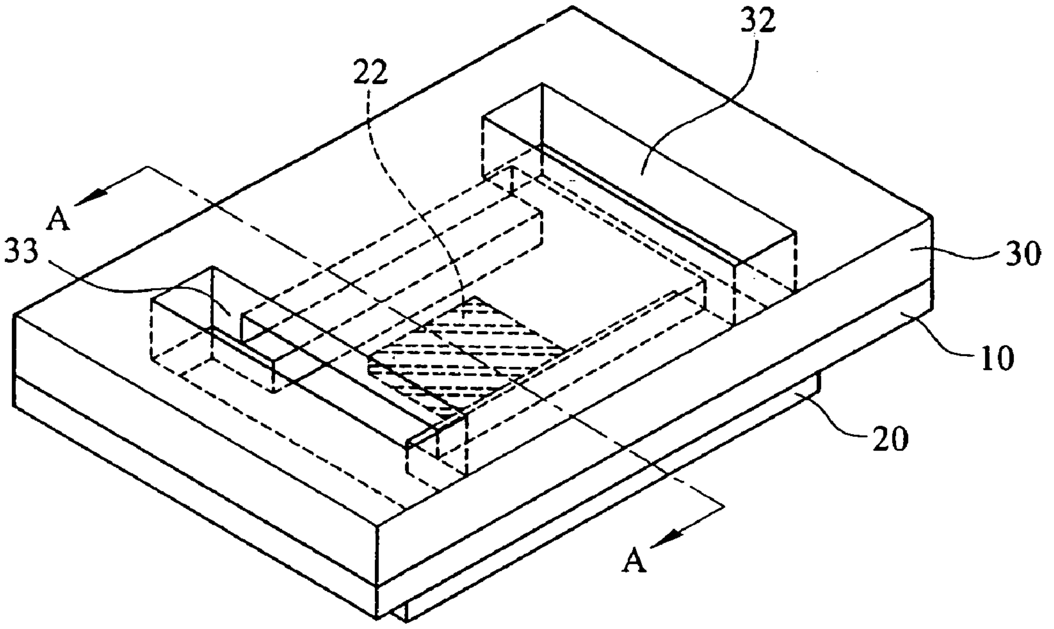
FIG. 2 is a perspective view of the biosensor package structure with the micro-fluidic channel according to the first embodiment of the present invention.

Referring to FIGS. 1 and 2, the present embodiment relates to a biosensor package structure with a micro-fluidic channel. The biosensor package structure includes a substrate 10, a biochip 20, and a cover 30.

Figure 3:
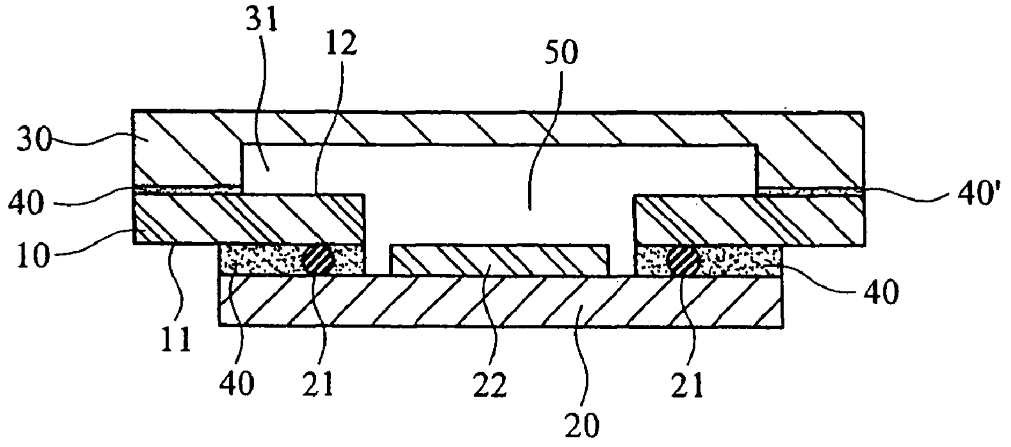
FIG. 3 is a cross-sectional view taken along line A-A of FIG. 2.

Referring to FIG. 3, the substrate 10 has a first surface 11, a second surface 12, and an opening 13 (as shown in FIG. 1). The first surface 11 is a lower surface of the substrate 10. The second surface 12 is an upper surface of the substrate 10. Moreover, a circuit (not shown) is formed on the first surface 11 of the substrate 10 to be in electrical connection with a circuit unit 21 of the biochip 20 and to be in signal connection with external circuits. Referring to FIG. 1 again, the opening 13 of the substrate 10 passes through the first surface 11 and the second surface 12 of the substrate 10, with a shape variable to meet different designs.

On the other hand, to satisfy practical needs, the substrate 10 is a flexible substrate or an inflexible substrate. In the case that the substrate 10 is flexible, the substrate 10 can be bent to match an environment of bioassay.

Referring to FIG. 1 again, the biochip 20 is designed upon principles related to genetic information of molecular biology, analytical chemistry and so on, and is capable of performing complex operation promptly like a semiconductor chip. The biochip 20 is typically defined with a bio-sensing area 22 where a biomedical sample to be sensed and assayed promptly and precisely.

Referring to FIGS. 2 and 3, the biochip 20 is attached on the first surface 11 of the substrate 10 by, for example, using an adhesive 40 to affix the biochip 20 to the first surface 11 of the substrate 10, so that the bio-sensing area 22 of the biochip 20 is exposed to the opening 13 of the substrate 10, allowing an introduced biomedical sample to pass through the bio-sensing area 22 of the biochip 20.

Referring to FIG. 1 again, the circuit unit 21 of the biochip 20 is a ball grid array (BGA). Referring to FIG. 3, in the case that the circuit unit 21 is embodied by the BGA, while the circuit unit 21 of the biochip 20 electrically connects with the circuit (not shown) on the substrate 10, the adhesive 40 is filled between the biochip 20 and the second surface 12 of the substrate 10 by the known underfill packaging process so as to isolate the circuit unit 21 from air as well as moisture and strengthen the whole structure, thereby preventing the biomedical sample from leaking through any interval between the biochip 20 and the substrate 10 and ensuring bioassay accuracy.

The cover 30 is made of a biocompatible material, such as polydimethylsiloxane (PDMS), polymethylmethacrylate (PMMA) or other polymers. For example, PDMS is a highly hydrophobic elastomer and possesses excellent biocompatibility as well as electrical isolation while serving to absorb vibration and reduce impaction from stress. Also, PDMS is unlikely to be affected by ambient temperature or moisture, and thus is a material suitable for biomedical applications.

As shown in FIGS. 1 and 3, the cover 30 is attached to the second surface 12 of the substrate 10. For instance, the cover 30 is attached to the second surface 12 of the substrate 10 by an adhesive 40' or by a surface treatment technique, such as an oxygen plasma treatment technique, so that the cover 30 and the opening 13 of the substrate 10 covered thereby together form a micro-fluidic channel 50. Furthermore, the cover 30 has a cavity 31, for example, a reversed U-shaped cover, so as to facilitate forming the micro-fluidic channel 50.

In addition, according to FIG. 1, the cover 30 is further provide with a sample inlet 32 and a sample outlet 33, which are both in communication with the cavity 31 of the cover 30 and the opening 13 of the substrate 10, so that the biomedical sample is introduced into the micro-fluidic channel 50 through the sample inlet 32 and then pass through the bio-sensing area 22 of the biochip 20, thereby achieving desired bioassay.

The cover 30 can be a light-transmitting cover or, for optical inspection of the biomedical sample, the cover 30 can be an opaque cover, so as to allow optical inspection through the cover 30. Also, to meet practical needs, the cover 30 is made of a flexible or inflexible material. In an embodiment where the cover 30 is flexible and operates in conjunction with the substrate 10 which is also made of a flexible material, the biosensor package structure can be manufacturing through the known tape carrier package (TCP) process widely used in packaging, so as to enable mass production of biosensors.

To smooth the flow of the biomedical sample and shorten assay time, the biosensor in the present embodiment is further equipped with a micro-fluidics driving unit for adjusting the flow rate of the biomedical sample. Examples of the micro-fluidics driving unit include, but are not limited to, a pneumatic micro-fluidics driving unit 60', a piezoelectric micro-fluidics driving unit 60", and the like. For example, in an embodiment of the biosensor package structure having the pneumatic micro-fluidics driving unit 60' as shown in FIGS. 4A and 4B, the pneumatic micro-fluidics driving unit 60' is disposed on the cover 30 of the biosensor package structure.

Figure 4A:
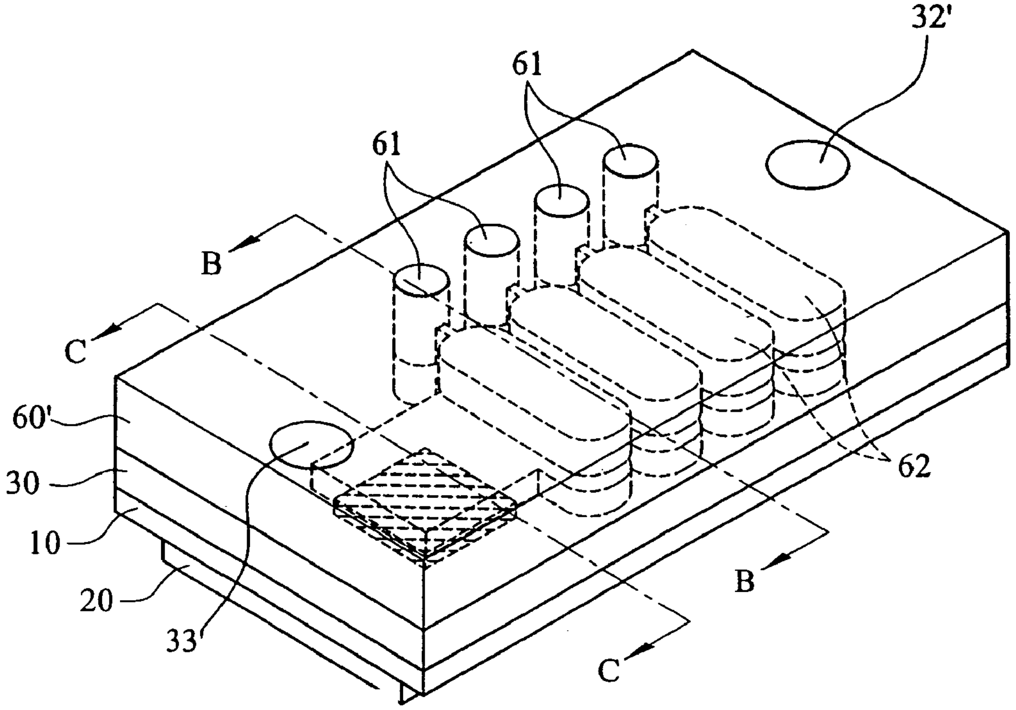
FIG. 4A is a perspective view of a biosensor package structure with a micro-fluidic channel according to a second embodiment of the present invention.
Figure 4B:
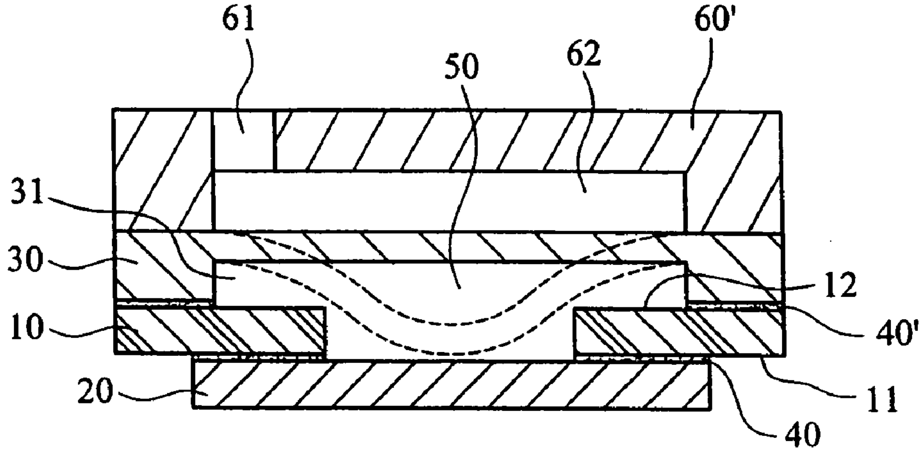
FIG. 4B is a cross-sectional view taken along line B-B of FIG. 4A.

Referring to FIGS. 4A and 4B, the pneumatic micro-fluidics driving unit 60' includes a sample inlet 32', a sample outlet 33', at least a gas inlet 61 and at least a gas tank 62. The sample inlet 32' and the sample outlet 33' are in communication with the sample inlet 32 (not shown) and the sample outlet 33 (not shown) of the cover 30 and also in communication with the cavity 31 of the cover 30 and the opening 13 (not shown) of the substrate 10, so that the biomedical sample is introduced into the micro-fluidic channel 50 through the sample inlet 32'.

Moreover, each said gas inlet 61 communicates with one said corresponding gas tank 62 but does not communicate with the micro-fluidic channel 50, so as to protect the biomedical sample from external contaminants. In the case that the cover 30 is flexible, and the pneumatic micro-fluidics driving unit 60' has a thickness greater than that of the cover 30 of the biosensor package structure, a high-pressure gas is introduced into the gas tank 62 through the gas inlet 61 so that pressure form the high-pressure gas deforms the cover 30 of the biosensor package structure to block the biomedical sample flowing in the micro-fluidic channel 50, thereby allowing the cover 30 to act as a valve for achieving flow rate control of the biomedical sample.

In a further preferred embodiment, the pneumatic micro-fluidics driving unit 60' has a plurality of said gas inlets 61 and gas tanks 62, and a high-pressure gas is introduced into each of the gas inlets 61 so as to deform corresponding portions of the cover 30 continuously and successively, in a way kind of like how a pump works, and exercise flow rate control over the biomedical sample in the micro-fluidic channel 50.

Figure 4C:
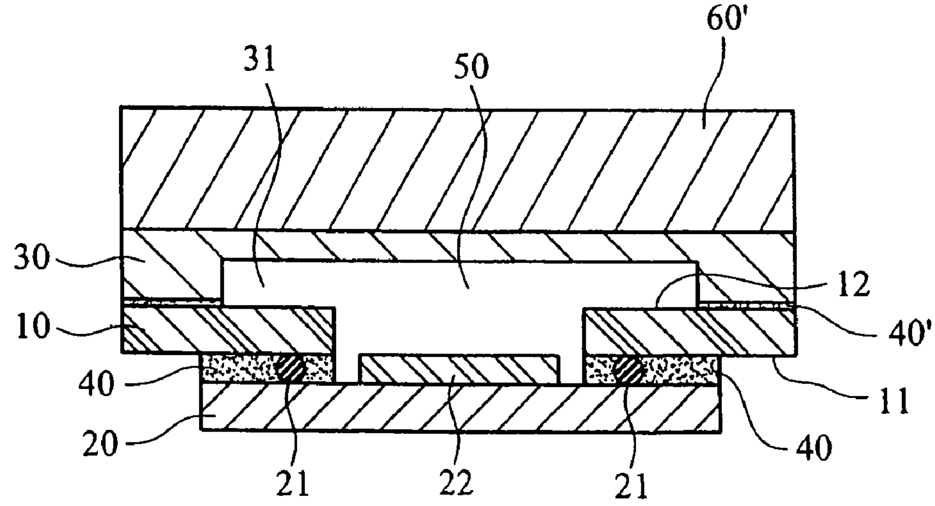
FIG. 4C is a cross-sectional view taken along line C-C of FIG. 4A.

According to FIGS. 4A and 4C, upon delivery of the biomedical sample to the biochip 20 by the pneumatic micro-fluidics driving unit 60', the biomedical sample reacts sufficiently at the bio-sensing area 22 of the biochip 20, so as for ion concentration of the biomedical sample to be measured.

Figure 5:
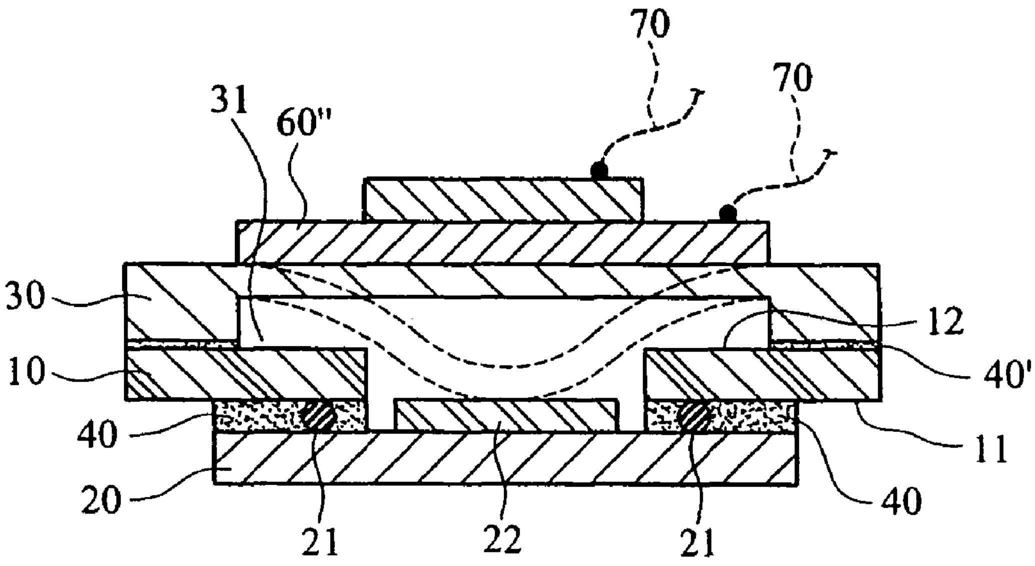
FIG. 5 is an applied view of the biosensor package structure of the present invention.

Referring now to FIG. 5, the micro-fluidics driving unit is, as described previously, the piezoelectric micro-fluidics driving unit 60" directly disposed on the cover 30 of the biosensor package structure and electrically connected to the cover 30 by means of wires 70. By adjusting an applied voltage, the piezoelectric micro-fluidics driving unit 60" is controlled to deform the cover 30 of the biosensor package structure to act as a valve so as to achieve flow rate control of the biomedical sample. Alternatively, a plurality of said piezoelectric micro-fluidics driving units 60" are provided on the cover 30 of the biosensor package structure and driven at different frequencies, so as to collectively function as a pump.

By implementing the embodiments of the present invention, the biosensor package structure with the micro-fluidic channel 50 is achieved by a way similar to the method for electronic packaging, so as to simplify the manufacturing process and enable mass production of the biosensor. Besides, the biosensor package structure with the micro-fluidic channel is realized by normal package materials that are readily available, so as to reduce manufacturing costs of the biosensor. Also, the embodiments of the present invention are advantageous by aligning the biosensor package structure with the existing electronic package structure in a technical respect. Consequently, the biosensor package structure of the embodiments of the present invention is extensively fit for circuit integration or biosensor applications such as cantilever biosensors, capacitive sensors, electrochemical electrodes sensors and so on.

Although the particular embodiments of the present invention have been described in detail for purposes of illustration, it will be understood by one of ordinary skill in the art that numerous variations will be possible to the disclosed embodiments without going outside the scope of the present invention as disclosed in the claims.

What is claimed is:

1. A biosensor package structure with a micro-fluidic channel, the biosensor package structure comprising:

an inflexible substrate having a first surface, a second surface, and an opening, wherein a circuit is formed on the first surface;

a biochip attached on the first surface and defined with a bio-sensing area totally exposed to the opening;

an adhesive that affixes the biochip to the first surface; and a cover having a cavity, a sample inlet, and a sample outlet, and the cover is attached on the second surface to cover the opening so that the cavity is in communication with the opening to form a micro-fluidic channel and the sample inlet and the sample outlet are both in communication with the cavity and the opening so that a biomedical sample is introduced into the micro-fluidic channel through the sample inlet and then pass through the bio-sensing area;

wherein the biochip has a ball grid array electrically connected with the circuit on the inflexible substrate, with the ball grid array placed on the same side as the bio-sensing area; and wherein the adhesive is filled between the biochip and the first surface by the underfill packaging process to surround the ball grid array.

2. The biosensor package structure of claim 1, wherein the cover is made of a biocompatible material.

3. The biosensor package structure of claim 1, wherein the cover is affixed to the second surface by an adhesive.

4. The biosensor package structure of claim 1, wherein the cover is a light-transmitting cover.

5. The biosensor package structure of claim 1, wherein the cover is an opaque cover.

6. The biosensor package structure of claim 1, wherein the cover is made of an inflexible material.

7. The biosensor package structure of claim 1, wherein the cover is made of a flexible material.

8. The biosensor package structure of claim 7, further comprising a micro-fluidic driving unit disposed on the cover.

9. The biosensor package structure of claim 8, wherein the micro-fluidic driving unit is a pneumatic micro-fluidic driving unit.

10. The biosensor package structure of claim 8, wherein the micro-fluidic driving unit is a piezoelectric micro-fluidic driving unit.

* * * * *